United States Patent
Markert-Hahn

(12) 
(10) Patent No.: US 8,137,937 B2
(45) Date of Patent: Mar. 20, 2012

(54) METHOD FOR BISULFITE TREATMENT

(75) Inventor: Christine Markert-Hahn, Penzberg (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 839 days.

(21) Appl. No.: 12/095,299

(22) PCT Filed: Dec. 12, 2006

(86) PCT No.: PCT/EP2006/011932
§ 371 (c)(1),
(2), (4) Date: May 28, 2008

(87) PCT Pub. No.: WO2007/068437
PCT Pub. Date: Jun. 21, 2007

(65) Prior Publication Data
US 2008/0281087 A1 Nov. 13, 2008

(30) Foreign Application Priority Data
Dec. 14, 2005 (EP) .................................... 05027329

(51) Int. Cl.
*C12P 19/34* (2006.01)
*C07H 21/00* (2006.01)

(52) U.S. Cl. ................... 435/91.2; 536/25.4; 536/25.41; 536/25.42

(58) Field of Classification Search ........................ None
See application file for complete search history.

(56) References Cited

U.S. PATENT DOCUMENTS

| | | | |
|---|---|---|---|
| 5,786,146 A | 7/1998 | Herman et al. | |
| 6,174,670 B1 * | 1/2001 | Wittwer et al. | ................... 435/6 |
| 6,331,393 B1 | 12/2001 | Laird et al. | |
| 7,501,240 B2 * | 3/2009 | Birkner et al. | ................... 435/6 |
| 2003/0152950 A1 | 8/2003 | Garner et al. | |
| 2004/0241704 A1 | 12/2004 | Markert-Hahn et al. | |

FOREIGN PATENT DOCUMENTS

| | | |
|---|---|---|
| EP | 1 394 173 B1 | 3/2004 |
| WO | WO 01/98528 A2 | 12/2001 |
| WO | WO 02/31186 A2 | 4/2002 |
| WO | WO 2004/067545 A1 | 8/2004 |
| WO | WO 2005/054502 A1 | 6/2005 |

OTHER PUBLICATIONS

Clark, S., et al., 1994, "High sensitivity mapping of methylated cytosines", *Nucleic Acids Research*, 22(15)2990-2997.
Feil, R., et al., 1994, "Methylation analysis on individual chromosomes: improved protocol for bisulfite-genomic sequencing", 22(4):695-696, Nucl. Acids Res.
Frommer, M., 1992, "A genomic sequencing protocol that yields a positive display of 5-methylcytosine residues in individual DNA strands", *Proc. Natl. Acad. Sci. USA*, 89:1827-1831.
Grigg, G., et al., 1994, "Sequencing 5-Methylcytosine Residues in Genomic DNA", *BioEssays*, 16(0:431436.
Grigg, G., 1996, "Sequencing 5-methylcytosine residues by the bisulfite method", *The Journal of Seq.&Mapping* 6:189-198.
Grunau, C., et al., 2001, "Bisulfite genomic sequencing: systematic investigation of critical experimental parameters", *Nucleic Acids Research*, 29 (13e65):1-7.
Komlyama, M., et al., 1994, "Catalysis of Diethylenetriamine for Bisulfite-Induced Deamination of Cytosine in Oligodeoxyribonucleotides", *Tetrahedron Letters*, 35(44):8185-8188.
Olek, A., et al., 1996, "A modified and improved method for bisulfite based cytosine methylation analysis", *Nucleic Acids Research*, 24(24):5064-5066.
Paulin, R., et al., 1998, "Urea improves efficiency of bisulfite-mediated sequencing of 5'-methylcytosine in genomic DNA", *Nucleic Acids Research*, 26(21):5009-5010.
Raizis, A., et al., 1995, "A Bisulfite method of 5-Methylcytosine Mapping That Minimizes Template Degradation", *Analytical Biochemistry*, 226:161-166.
Warneck, P., et al. 2002, "Identification and resolution of artifacts in bisulfite sequencing", *Methods*, 27:101-107.

* cited by examiner

*Primary Examiner* — Lawrence E Crane
(74) *Attorney, Agent, or Firm* — Olga Kay

(57) ABSTRACT

The present application is directed to a method for performing a bisulfite reaction to determine methylation positions in a nucleic acid via treatment of the solid phase-bound nucleic acid with bisulfite, desulfonation and elution of the nucleic acid from the solid phase.

16 Claims, No Drawings

METHOD FOR BISULFITE TREATMENT

CROSS-REFERENCE TO RELATED APPLICATIONS

This application is a national stage of the international application PCT/EP2006/011932, filed on Dec. 12, 2006 and claiming priority to a European application 05027329.1 filed on Dec. 14, 2005.

The present application is directed to a method for performing a bisulfite reaction to determine methylation positions in a nucleic acid, i.e. methylated and non-methylated cytosines. In this method, the nucleic acid is bisulfite treated and is bound to a solid phase when an alkaline solution is added for desulfonation and elution of the nucleic acid from the solid phase. The nucleic acid can be amplified in an additional step. The solid phase is preferably a material comprising glass or silica, more preferably a glass fleece, glass membrane or a magnetic glass particle. Further, several uses of the alkaline solution for bisulfite treatment are disclosed and a kit containing a bisulfite reagent, a solid phase and an alkaline solution.

BACKGROUND OF THE INVENTION

Genes constitute only a small proportion of the total mammalian genome, and the precise control of their expression in the presence of an overwhelming background of noncoding desoxyribonucleic acid (DNA) presents a substantial problem for their regulation. Noncoding DNA, containing introns, repetitive elements, and potentially active transposable elements require effective mechanisms for its long term silencing. Mammals appear to have taken advantage of the possibilities afforded by cytosine methylation to provide a heritable mechanism for altering DNA-protein interactions to assist in such silencing. DNA methylation is essential for the development of mammals; and plays a potential role during aging and cancer. The involvement of methylation in the regulation of gene expression and as an epigenetic modification marking imprinted genes is well established. In mammals, methylation occurs only at cytosine residues and more specifically only on cytosine residues adjacent to a guanosine residue, i.e. at the sequence CG. The detection and mapping of DNA methylation sites are essential steps towards understanding the molecular signals which indicate whether a given sequence is methylated.

This is currently accomplished by the so-called bisulfite method described by Frommer, M., et al., Proc Natl Acad Sci USA 89 (1992) 1827-31 for the detection of 5-methyl-cytosines. The bisulfite method of mapping 5-methylcytosine uses the effect that sodium hydrogen sulfite reacts with cytosine but not or only poorly with 5-methyl-cytosine. Cytosine reacts with bisulfite to form a sulfonated cytosine reaction intermediate being prone to deamination resulting in a sulfonated uracil which can be desulfonated to uracil under alkaline conditions. It is common knowledge that uracil has the base pairing behavior of thymine different to the educt cytosine whereas 5-methylcytosine has the base pairing behavior of cytosine. This makes the discrimination of methylated or non-methylated cytosines possible by e.g. bisulfite genomic sequencing (Grigg, G., and Clark, S., Bioessays 16 (1994) 431-6; Grigg, G. W., DNA Seq 6 (1996) 189-98) or methylation specific PCR (MSP) disclosed in U.S. Pat. No. 5,786,146.

There are various documents addressing specific aspects of the bisulfite reaction (Benyajati, C., et al., Nucleic Acids Res 8 (1980) 5649-67) make general investigations to the bisulfite modification of 5-methyl-deoxycytosine and deoxycytosine (Olek, A., et al., Nucleic Acids Res 24 (1996) 5064-6) disclose a method for bisulfite base sequencing whereby bisulfite treatment and subsequent PCR steps are performed on material embedded in agarose beads. In the bisulfite method as disclosed by Clark, S. J., et al., Nucleic Acids Res 22 (1994) 2990-7, the sample is desalted after deamination.

Raizis, A. M., et al., Anal Biochem 226 (1995) 161-6 disclose a bisulfite method of 5-methylcytosine mapping that minimizes template degradation. They investigate the influence of pH, temperature and time of reaction. Similar investigations have been made by Grunau, C., et al., Nucleic Acids Res 29 (2001) 13e65:1-7 or Warnecke, P. M., et al., Methods 27 (2002) 101-7. Different additional components in the bisulfite mixture are disclosed by WO 01/98528 or by Paulin, R., et al., Nucleic Acids Res 26 (1998) 5009-10. An additional bisulfite step after bisulfite treatment and PCR is disclosed in WO 02/31186. Komiyama, M., and Oshima, S., Tetrahedron Letters 35 (1994) 8185-8188) investigate the catalysis of bisulfite-induced deamination of cytosine in oligodeoxyribonucleotides.

Kits for performing bisulfite treatments are commercially available from Intergen, distributed by Serologicals Corporation, Norcross, Ga., USA, e.g. CpGenome™ DNA modification kit or CpGenome™ Fast DNA Modification Kit. Another commercial kit is the EZ DNA-Methylation-Gold Kit available from Zymo Research Inc., Orange, Calif., USA. These kits provide sequential procedures comprising denaturation of purified DNA or crude lysate, deamination of DNA, desalting (=washing with a buffer that ensures the DNA to be bound to the solid phase) of deaminated DNA after binding of DNA to a solid phase, desulfonation of bound desaminated DNA by adding of alkaline, washing the DNA to remove alkaline and elution of DNA with a neutral buffer. The eluate or part of it is then usually used for PCR.

Another variation of the bisulfite genomic sequencing method is disclosed by Feil, R., et al., Nucleic Acids Res 22 (1994) 695-6, whereby the genomic DNA is bound to glass beads after deamination and washed. After elution the nucleic acid is desulfonated. It is known that nucleic acids can be isolated by the use of their binding behavior to glass surfaces, e.g. adsorption to silica gel or diatomic earths, adsorption to magnetic glass particles (MGPs) or organo silane particles under chaotropic conditions. Extraction using solid phases usually contains the steps of adding the solution with the nucleic acids to the solid phase under conditions allowing binding of the substance of interest to the solid phase, removal of the remainder of the solution from the solid phase bound nucleic acids and subsequent release of the nucleic acids from the solid phase into a liquid eluate (sometimes called elution). The result of such process is usually a solution containing the substance of interest in dissolved state.

Still another variation of the bilsulfite method is disclosed by US 2004/0241704 or EP 1 394 173. Therein a bisulfite treatment is disclosed wherein the nucleic acid is bound to a solid phase during all or only some of the steps of the bisulfite reaction.

SUMMARY OF THE INVENTION

The problem to be solved by the present invention was to provide a method which is automatable.

The problem discussed above is solved by providing a method for the conversion of a cytosine base, preferably cytosine bases, in a nucleic acid to an uracil base, preferably uracil bases, whereby preferably 5-methyl-cytosine bases are not significantly converted ("bisulfite reaction" or "bisulfite treatment") comprising the steps of
a1) binding the nucleic acid to a solid phase and incubating the solid phase bound nucleic acid in the presence of sulfite ions thereby deaminating the cytosine base in the nucleic acid, or
a2) incubating the nucleic acid in the presence of sulfite ions thereby deaminating the cytosine base in the nucleic acid and binding the nucleic acid to a solid phase,
b) optionally washing the solid phase bound nucleic acid,
c) incubating the solid phase bound nucleic acid in a solution with an alkaline pH thereby
  desulfonating the cytosine base in the nucleic acid and converting it to an uracil base and
  eluting the nucleic acid.

In another embodiment of the invention, a method is provided for the amplification of a nucleic acid comprising the steps of
a1) binding the nucleic acid to a solid phase and incubating the solid phase bound nucleic acid in the presence of sulfite ions thereby deaminating the cytosine base in the nucleic acid, or
a2) incubating the nucleic acid in the presence of sulfite ions thereby deaminating the cytosine base in the nucleic acid and binding the nucleic acid to a solid phase,
b) optionally washing the solid phase bound nucleic acid,
c) incubating the solid phase bound nucleic acid in a solution with an alkaline pH thereby
  desulfonating the cytosine base in the nucleic acid and converting it to an uracil base and
  eluting the nucleic acid,
d) amplifying the eluted nucleic acid.

The invention allows the automatization of the process by combining the desulfonation with the elution step. After having desalted the bound deaminated DNA, there is no separate desulfonation step by adding alkaline, subsequent washing and elution at the end, but there is just elution with an alkaline solution, preferably 20 to 60 mM NaOH. The eluate can then be used directly for amplification of the nucleic acid. By simplifying the workflow, it becomes similar regarding the steps, not the reagents, with a classical DNA purification process when the solution containing the deaminated DNA is seen as the "sample material" for DNA purification comprising binding, washing and elution steps. Therefore, the process can be automated using DNA products that are on the market with only minor reagent modifications.

In another embodiment of the invention, a solution comprising 10 to 100 mM, preferably 20 to 60 mM, NaOH or KOH is used for the desulfonation of a sulfonated and deaminated cytosine base in a nucleic acid or for the desulfonation of a sulfonated and deaminated cytosine base in a solid phase bound nucleic acid and the subsequent elution of the solid-phase bound nucleic acid from the solid phase.

In another embodiment of the invention, a kit for performing a bisulfite reaction is provided comprising
  a bisulfite salt or a solution comprising bisulfite ions,
  a solid phase, and
  a solution comprising 10 to 100 mM, preferably 20 to 60 mM, NaOH or KOH.

A "nucleic acid" is a polymeric compound of "nucleotides" as known to the expert skilled in the art. It is used herein to denote a "nucleic acid" in a sample which should be analyzed, i.e. the presence, non-presence or amount thereof in a sample should be determined. Therefore, in other words the "nucleic acid" is the target and can therefore be also denoted as "target nucleic acid". For example, if it has to be determined whether blood contains the human immunodeficiency virus, the "target nucleic acid" is the nucleic acid of the human immunodeficiency virus or more specifically the nucleic acid sequence, i.e. the order of the bases adenine, guanine, cytosine or thymine, that is determined. More specifically in the context of the invention, the "target nucleic acid" is genomic DNA that may comprise methylated-cytosine bases in CpG sites. After "bisulfite treatment" the nucleic acid sequence of the genomic DNA is changed depending on methylation as non-methylated bases are converted to uracil bases and the changed nucleic acid sequence is determined.

As is known in the art, a "nucleoside" is a base-sugar combination. The base portion of the nucleoside is normally a heterocyclic base. The two most common classes of such heterocyclic bases are the purines and the pyrimidines, in more detail the adenine (A), guanine (G), thymine (T) or cytosine (C) base. The uracil base is naturally contained in the ribonucleic acid. Another naturally occurring base is 5-methyl-cytosine or methyl-cytosine, which is cytosine which is substituted by a methyl group at the 5-position of the aromatic ring of the base.

"Nucleotides" are "nucleosides" that further include a phosphate group covalently linked to the sugar portion of the nucleoside. For those "nucleosides" that include a pentofuranosyl sugar, the phosphate group can be linked to either the 2', 3' or 5' hydroxyl moiety of the sugar. A "nucleotide" is the "monomeric unit" of an "oligonucleotide", more generally denoted herein as an "oligomeric compound", or a "polynucleotide", more generally denoted as a "polymeric compound". Another general expression therefor is deoxyribonucleic acid (DNA) and ribonucleic acid (RNA).

According to the invention, an "oligomeric compound" is a compound consisting of "monomeric units" which may be "nucleotides" alone or "non-natural compounds" (see below), more specifically "modified nucleotides" (or "nucleotide analogs") or "non-nucleotide compounds", alone or combinations thereof. "Oligonucleotides" and "modified oligonucleotides" (or "oligonucleotide analogs") are subgroups of "oligomeric compounds" in the context of the invention.

In the context of this invention, the term "oligonucleotide" refers to "polynucleotides" formed from a plurality of "nucleotides" as the "monomeric unit", i.e. an "oligonucleotide" belongs to a specific subgroup of a "oligomeric compound" or "polymeric compound" of ribonucleic acid (RNA) or deoxyribonucleic acid (DNA) with "monomeric units". The phosphate groups are commonly referred to as forming the internucleoside backbone of the "oligonucleotide". The normal linkage or backbone of RNA and DNA is a 3' to 5' phosphodiester linkage.

"Oligonucleotides" and "modified oligonucleotides" (see below) according to the invention may be synthesized as principally described in the art and known to the expert in the field. Methods for preparing oligomeric compounds of specific sequences are known in the art, and include, for example, cloning and restriction of appropriate sequences and direct chemical synthesis. Chemical synthesis methods may include, for example, the phosphotriester method described by Narang, S. A., et al., Methods Enzymol. 68 (1979) 90-98, the phosphodiester method disclosed by Brown, E. L., et al., Methods Enzymol. 68 (1979) 109-151, the phosphoramidite method disclosed in Beaucage, S. L., and Caruthers, M. H., Tetrahedron Lett. 22 (1981) 1859-1862, the H-phosphonate method disclosed in Garegg, P. J., et al., Chem. Scr. 25 (1985) 280-282 and the solid support method disclosed in U.S. Pat. No. 4,458,066.

As said above, a "nucleic acid" as well as the "target nucleic acid" is a polymeric compound of "nucleotides" as known to the expert skilled in the art. It is used herein to denote a "nucleic acid" in a sample which should be analyzed, i.e. the presence, non-presence or amount thereof in a sample should be determined.

The term "primer" is used herein as known to the expert skilled in the art and refers to "oligomeric compounds" primarily to "oligonucleotides" but also to "modified oligonucleotides" that are able to "prime" DNA synthesis by a template-dependent DNA polymerase, i.e. the 3'-end of the e.g. oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except for the intended function—no fundamental difference between a "primer", an "oligonucleotide" or a "probe" according to the invention.

The term "probe" refers to synthetically or biologically produced nucleic acids (DNA or RNA) which, by design or selection, contain specific nucleotide sequences that allow them to hybridize under defined predetermined stringencies specifically (i.e., preferentially) to "target nucleic acids". A "probe" can be identified as a "capture probe" meaning that it "captures" the target nucleic acid so that it can be separated from undesirable materials which might obscure its detection. Once separation is accomplished, detection of the captured "target nucleic acid" can be achieved using a suitable procedure. "Capture probes" are often already attached to a solid phase. A specific example therefor is the microarray situation wherein a multitude of "capture probes" are attached to a "solid phase" which "capture" labeled cRNA or cDNA.

According to the invention the term a "bisulfite reaction", "bisulfite treatment" or "bisulfite method" shall mean a reaction for the conversion of a cytosine base, in particular cytosine bases, in a nucleic acid to an uracil base, or bases, preferably in the presence of bisulfite ions whereby preferably 5-methyl-cytosine bases are not significantly converted. This reaction for the detection of methylated cytosines is described in detail by Frommer et al., supra and Grigg and Clark, supra. The bisulfite reaction contains a deamination step and a desulfonation step (see FIG. 1; Grigg and Clark, supra). The statement that 5-methyl-cytosine bases are not significantly converted shall only take the fact into account that it cannot be excluded that a small percentage of 5-methyl-cytosine bases is converted to uracil although it is intended to convert only and exclusively the (non-methylated) cytosine bases (Frommer et al., supra).

The terms "methyl-cytosine base", "methylcytosine base", "methylated cytosine base" and "5-methyl-cytosine base" are used interchangeably throughout the application and shall denote the derivative of a cytosine base whereby a methyl group is attached to the C5 atom of the cytosine ring. A cytosine base is shown in the left part of FIG. 1. The term "non-methylated cytosine base" shall denote an underivatized cytosine base whereby no methyl group is attached to the C5 atom of the cytosine ring in contrast to the "methyl-cytosine base".

DETAILED DESCRIPTION OF THE INVENTION

Conventional techniques of molecular biology and nucleic acid chemistry, which are within the skill of the art, are explained in the literature. See, for example, Sambrook, J., et al., Molecular Cloning: A Laboratory Manual, Cold Spring Harbor Laboratory Press, Cold Spring Harbor, N.Y., 1989, Gait, M. J., ed., 1984; Hames, B. D., and Higgins, S. J., Nucleic Acid Hybridisation, a practial approach, IRL Press, Oxford, England (1985); and a series, Methods in Enzymology, Academic Press, Inc., all of which are incorporated herein by reference. All patents, patent applications, and publications mentioned herein, both supra and infra, are incorporated herein by reference.

In an embodiment of the invention, a method for the conversion of a cytosine base in a nucleic acid to an uracil base is provided comprising the steps of a1) binding the nucleic acid to a solid phase and incubating the solid phase bound nucleic acid in the presence of sulfite ions thereby deaminating the cytosine base in the nucleic acid, or a2) incubating the nucleic acid in the presence of sulfite ions thereby deaminating the cytosine base in the nucleic acid and binding the nucleic acid to a solid phase, b) optionally washing the solid phase bound nucleic acid, c) incubating the solid phase bound nucleic acid in a solution with an alkaline pH thereby
desulfonating the cytosine base in the nucleic acid and converting it to an uracil base and
eluting the nucleic acid.

The expert skilled in the art knows how to perform the bisulfite reaction in particular the deamination step of the bisulfite reaction, i.e. step a1) or step a2) of the method according to the invention, e.g. by referring to Frommer et al., supra or Grigg and Clark, supra who disclose the principal parameters of the bisulfite reaction. From Grunau et al., supra, it is known to the expert in the field what variations of the bisulfite method are possible. The influence of incubation time and temperature on deamination efficiency and parameters affecting DNA degradation is disclosed. In summary, in the deamination step a buffer containing bisulfite ions and optionally chaotropic agents as guanidinium ions or urea and further reagents as an alcohol or stabilizers as hydroquinone are employed and the pH is in the acidic range. The concentration of bisulfite is between 0.1 to 8 M bisulfite, preferably 0.1 to 6 M, more preferably 0.1 M to 5.5 M, the concentration of the chaotropic agent is between 1 to 8 M, whereby in general preferably guanidinium salts are employed, more preferably guanidinium hydrogen sulfite as described in WO 2005/054502. The pH is in the acidic range, preferably between 4.5 to 6.5, the temperature is between 0° C. to 90° C., preferably between room temperature (25° C.) to 90° C., and the reaction time is between 30 min to 24 hours or 48 hours or even longer, but preferably between 1 hour to 24 hours.

Therefore, in a preferred embodiment of the invention, a method is provided wherein in step a1) or a2) of the method according to the invention the presence of sulfite ions in the sample converts the (non-methylated) cytosine base in the methylated target nucleic acid in the sample into the uracil base. More preferably, the method comprises in step a1) or a2) the substeps of 1) mixing the sample comprising the methylated target nucleic acid with a solution comprising sulfite ions; 2) incubating the solution obtained in step 1) comprising the (methylated target) nucleic acid and sulfite ions whereby the target nucleic acid is deaminated, 3) optionally desalting the deaminated nucleic acid. The concentration of sulfite ions is preferably 0.1 to 8 M, more preferably 0.1 to 6.25 M, 0.1 to 6 M, more preferably 2 to 6 M. The pH of the solutions in step 1) and 2) is preferably in the acidic range, more preferably between 4.5 to 6.5. The incubation temperature in step 2) and 3) is preferably between 0° C. to 90° C., preferably between 18° C. to 90° C. The incubation time in step 2) is preferably between 30 min to 48 hours, more preferably 24 hours.

In a preferred embodiment of the invention, the incubation parameters as described in WO 2004/067545 may be used, wherein the nucleic acid is incubated in a solution for a time period of 1.5 to 3.5 hours at a temperature between 70 and 90° C., whereby the concentration of bisulfite in the solution is between 3 M and 6.25 M and whereby the pH value of the solution is between 5.0 and 6.0 whereby the nucleic acid is deaminated.

In step c) of the method of the invention, the solid phase bound nucleic acid is incubated in a solution with an alkaline pH. Thereby, the cytosine base in the nucleic acid is desulfonated and converted to an uracil base and the nucleic acid is eluted. This shall only mean that these effects happen in the same step or concurrently but it does not exclude that in a short time span elution and then desulfonation happens or vice versa. It shall only exemplify that these effects happen at the same time or connected to one another and not independently, in particular at points in time that are very far away from one another.

Preferably, the solution with an alkaline pH is a low concentrated aqueous solution, i.e. it contains a low total concentration of substances dissolved therein, preferably less than 200 mM, more preferably less than 100 mM. It is important that it still allows desulfonation but also elution. More preferably, the solution comprises NaOH. More preferably, the solution comprises 10 to 100 mM, preferably 20 to 60 mM, more preferably 25 to 50 mM, NaOH or KOH. 25 to 50 mM NaOH is preferred throughout this invention. It is evident to the expert skilled in the art that other substances than only NaOH or KOH can be used as e.g. LiOH or other alkali hydroxides. Also earth alkali hydroxides are feasible or substances that do not prevent elution of the nucleic acid and make the solution satisfyingly alkaline. The pH of the solution is preferably more than 10, more preferably more than 12 or 14. Other substances as stabilizers of the nucleic acid solution are possible as long as they do not interfere with the process or become degraded itself.

The elution and desulfonation can also be performed between room temperature (20° C.) and 85° C. Preferred is however an elevated temperature in the range between 60 to 80° C. as the elution is often more efficient at higher temperatures (see e.g. WO 99/16781). Therefore, in a more preferred embodiment of the invention, the temperature in step c) of the method of the invention is between 60 to 80° C. The desulfonation is not influenced very much by the temperature insofar as the reaction success itself is influenced. The temperature ranges for desulfonation is described herein under the description of the conditions for the bisulfite treatment.

In an embodiment of the invention, the nucleic acid is deoxyribonucleic acid (DNA), in particular genomic DNA, i.e. the DNA or nucleic acid which is found in the organism's genome and is passed on to offspring as information necessary for survival. The phrase is used to distinguish between other types of DNA, such as found within plasmids. The source of the nucleic acid may be eukaryotic or prokaryotic, preferably from vertebrates, particularly from mammalians, most preferred from animals or humans. Preferably, the nucleic acid is a methylated nucleic acid or methylated target nucleic acid in other words, i.e. it is a nucleic acid that contains or may contain a 5-methyl-cytosine base and contains or may contain a cytosine base.

The use of a solid phase during the deamination and/or desulfonation step of the bisulfite reaction has the advantage that the handling is simpler and/or easily amenable to automation. For example, when glass fleeces are used for the deamination and/or desulfonation steps, no time consuming DNA precipitation reactions are necessary; bound-free separation can easily be achieved by centrifugation, the dead volume of glass fleece is neglectable and therefore washing steps are very effective. This is an advantage when the bisulfite treatment DNA is used for PCR where potential inhibitors can reduce the sensitivity significantly. The method according to the invention can also be performed manually and is therefore suited for smaller laboratories where routine analyzers are not available. For larger laboratories with higher sample throughput, the use a solid phase that can be handled by routine analyzers, in particular magnetic glass particles, is advantageous.

In an embodiment of the invention, the nucleic acid is bound to a solid phase, which is unmodified, i.e. the nucleic acid is directly bound without any compound mediating the binding to the solid phase. The nucleic acid binds to the unmodified surface of the solid phase, whereby binding to the surface shall also take into account that the solid phase may contain pores and that the nucleic acid may be bound to surfaces in pores of the solid phase. In embodiments according to the invention, the solid phase may be an ion exchanger (commercially available from e.g. Amersham Biosciences Europe, Freiburg, Germany), able to bind a nucleic acid under specific conditions, hydroxylapatite (commercially available from Sigma, Taufkirchen, Germany), glass or silica or materials comprising glass or silica, preferably with an unmodified surface. In another embodiment the solid phase may be modified, i.e. the solid phase indirectly binds the nucleic acid with a compound mediating the binding to the solid phase, e.g. by sequence specific binding of the nucleic acid to oligonucleotides attached to the surface or streptavidin (attached to the surface of the solid phase) binding to biotin-labeled DNA. Suitable particles therefore are commercially available from DYNAL, Oslo, Norway and described e.g. in WO 90/06045.

The term "unmodified" shall mean that there is no further chemical modification, i.e. no other chemical groups are attached covalently or non-covalently. The term "unmodified surface", "unmodified silica surface" or "unmodified glass surface" shall mean that no other chemical groups are attached covalently or non-covalently which serve as an intermediary substance for nucleic acid binding and where the nucleic acids bind to the intermediary substance and not to the silica surface itself. Therefore, the nucleic acids bind preferably by hydrogen bonding and other atomic forces directly to the "unmodified surface". An example of a modified surface are silica surfaces to which oligonucleotides are attached which bind in sequence-specific manner nucleic acid molecules. Another example for modified silica surfaces are silica surfaces coated with streptavidin which binds to biotinylated DNA molecules.

In a particularly preferred embodiment according to the invention, the solid phase is a material comprising glass or silica, preferably with an unmodified (glass or silica) surface, e.g. glass fibers or, diatomaceous earth, glass beads or particles, glass membranes or magnetic glass particles or other substances covered with an unmodified glass surface. Particularly preferred are glass fleeces or glass membranes or magnetic glass particles. Such solid phases are disclosed e.g. in EP 0 389 063 or U.S. Pat. No. 5,234,809.

The conditions for binding DNA or nucleic acids to glass or silica surfaces are basically known to the expert in the field. These processes are described in detail by various documents. In Vogelstein, B., and Gillespie, D., Proc Natl Acad Sci USA 76 (1979) 615-9, for instance, a procedure for binding nucleic acids from agarose gels in the presence of sodium iodide to ground flint glass is proposed. The purification of plasmid DNA from bacteria on glass dust in the presence of sodium perchlorate is described in Marko, M. A., et al., Anal Biochem 121 (1982) 382-7. In DE 37 34 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing Tris/EDTA buffer. A similar procedure for purifying DNA from lambda phages is described in Jakobi, R., et al., Anal Biochem 175 (1988) 196-201. The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. This is a limiting step, however, that prevents the procedure from being used to process large quantities of samples. In a preferred embodiment of the invention, magnetic glass particles are used to bind the nucleic acids after precipitation by adding salt and ethanol as described e.g. in Alderton, R. P., et al., Anal Biochem 201 (1992) 166-9 and PCT GB 91/00212.

In a very preferred embodiment of the invention, the solid phase is a magnetic glass particle, preferably with an unmodified glass surface. The magnetic glass particles are a solid dispersion of small magnetic cores in glass, i.e. they are glass droplets in which very small magnetic objects are dispersed. Those objects that are referred to as magnetic are drawn to a magnet, i.e. ferri- or ferromagnetic or superparamagnetic materials for instance. Preferred are ferri- or ferromagnetic materials, in particular if they have not yet been premagnetized. Preferred magnetic materials are iron or iron oxide as e.g. magnetite ($Fe_3O_4$) or $Fe_2O_3$, preferably $\gamma$-$Fe_2O_3$. In principle, barium ferrite, nickel, cobalt, Al—Ni—Fe—Co alloys or other ferri- or ferromagnetic material could be used. Particularly preferred according to the present invention are the magnetic glass particles described in WO 96/41811, WO 00/32762 and WO 01/37291.

The magnetic glass particles used in the present invention may be provided in different formulations essentially as described in WO 01/37291. It is possible to provide them in the form of a tablet, as a powder or preferably as a suspension. In a preferred embodiment of the invention these suspensions contain between 5 to 60 mg/ml magnetic glass particles (MGPs). In another embodiment of the invention the silica-containing material is suspended in aqueous buffered solutions which may optionally contain a chaotropic agent in a concentration of between 2 and 8 mol/l, and preferably between 4 and 6 mol/l. Chaotropic salts are sodium iodide, sodium perchlorate, guanidinium thiocyanate, guanidinium isothiocyanate or guanidinium hydrochloride. A chaotropic agent according to the present invention is any chemical substance which will disturb the ordered structure of liquid water and will have the effect that DNA or RNA will bind to the MGPs according to the present invention if this agent is present in the DNA or RNA containing solution. Other compounds known to the expert in the field are also possible.

The most preferred MGPs according to the invention are manufactured according to the international application WO 01/37291 which are also provided in the MagNA Pure LC DNA Isolation Kit I (Roche, Mannheim, Germany). They are produced by the sol-gel-method as described in the international application WO 01/37291 using magnetic objects or pigments with a diameter of about 23 nm (manufactured by CERAC consisting of $\gamma$-$Fe_2O_3$; CERAC: P.O. Box 1178, Milwaukee, Wis. 53201-1178 USA; Article-No. I-2012). Therefore, in a preferred embodiment of the invention, the magnetic glass particle has a mean diameter between 0.5 µm and 5 µm. In another embodiment of the invention, the magnetic glass particle contains a magnetic object with a diameter between 5 and 500 nm. In yet another preferred embodiment of the invention, the magnetic glass particle is manufactured by the sol-gel method.

The experimental procedure for binding the nucleic acid to unmodified glass or silica surfaces (of preferably the magnetic glass particles) can be described in detail as follows. It is preferably performed in the presence of chaotropic salts with a concentration of between 1 and 8 mol/l, and preferably between 2 and 6 mol/l. Chaotropic salts can be sodium iodide, sodium perchlorate, guanidinium thiocyanate, guanidinium isothiocyanate or guanidinium hydrochloride. A chaotropic agent according to the present invention is any chemical substance which disturbs the ordered structure of liquid water and has the effect that DNA (or RNA) binds to the magnetic glass particles if this agent is present in the DNA (or RNA) containing solution. Other biological substances known to the expert in the field may also be present. Still other substances are also possible. To bind the mixture of nucleic acids and optionally other biological compounds, the glass beads with an unmodified glass surface are added to the mixture and incubated for a period of time sufficient for the binding to occur. Experts are usually familiar with the duration of the incubation step. This step can be optimized by determining the quantity of immobilized nucleic acids on the surface at different points in time. Incubation times of between 10 seconds and 30 minutes can be appropriate for nucleic acids. Then the reagents for performing the different steps of the bisulfite reaction are added (or may even have been present before). After incubation or washing, the nucleic acids may separated from the liquid. This may be achieved in general by gravity or in the convenient case of nucleic acids bound to magnetic glass particles by separating the nucleic acid bound to the magnetic glass particles by applying a magnetic field. For instance, the magnetic particles can be pulled to the wall of the vessel in which incubation was performed. The liquid containing the biological compounds or reaction components that were not bound to the magnetic particles can then be removed. The removal procedure used depends on the type of vessel in which incubation was performed. Suitable steps include removing the liquid via pipeting or aspiration. The material with the bound nucleic acid may then be washed at least once, preferably with a mixture of 70 volume parts ethanol with 30 volume parts water ("70% Ethanol") or in an acidic wash solution as described in WO 99/40098. A wash solution is used that does not cause the nucleic acids and the target nucleic acid to be released from the material surface but that washes away the undesired contaminants as thoroughly as possible. This wash step preferably takes place by incubating the glass or silica with the bound nucleic acid. The material is preferably re-suspended during this step. The contaminated wash solution is preferably removed just as in the binding step described above. After the last wash step, the material can be dried briefly in a vacuum, or the fluid can be allowed to evaporate. A pretreatment step using acetone may also be performed.

In an embodiment of the invention the nucleic is obtained from a biological sample using the solid phases according to the invention and methods known to the expert in the field. The biological sample comprises cells from multicellular organisms as e.g. human and animal cells such as Leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. In a preferred embodiment of the invention the biological sample is a fluid from the human or animal body. Preferably the biological sample is blood, blood plasma, blood serum or urine. The blood plasma is preferably EDTA-, heparin- or citrate-treated blood plasma. The biological sample comprising the nucleic acids is lysed to create a mixture of biological compounds comprising nucleic acids and other components. Procedures for lysing biological samples are known by the expert and can be chemical, enzymatic or physical in nature. A combination of these procedures is applicable as well. For instance, lysis can be performed using ultrasound, high pressure, shear forces, alkali, detergents or chaotropic saline solutions, or proteases or lipases. For the lysis procedure to obtain nucleic acids, special reference is made to Sambrook et al.: Molecular Cloning, A Laboratory Manual, 2nd Edition, Cold Spring Harbour Laboratory Press, Cold Spring Harbour, N.Y. and Ausubel et al.: Current Protocols in Molecular Biology 1987, J. Wiley and Sons, NY. Then the nucleic acids are isolated from the lysis mixture using the methods and solid phases according to the invention and can then be subjected to the methods according to the invention, i.e. the bisulfite treatment according to the invention. Chaotropic agents are also used to lyse cells to prepare a mixture between nucleic acids and other biological substances (see e.g. Sambrook et al. (1989) or EP 0 389 063). Afterwards the material comprising glass or silica is added and a purification effect results from the behavior of DNA or RNA to bind to material with a glass surface under these conditions i.e. in the presence of certain concentrations of a chaotropic agent, higher concentrations of organic solvents or under acidic conditions. Therefore, the present invention also considers the combination of lysis steps and the bisulfite reaction, i.e. the nucleic acid isolated from the mixture between nucleic acids and other biological substances is directly subjected to the bisulfite treatment whereby the nucleic acid is bound to a solid phase during the deamination and/or the desulfonation step.

In more detail, a method is provided wherein the nucleic acid is isolated from a mixture of a nucleic acid and other biological compounds and bound to a solid phase during the deamination and the desulfonation step of the bisulfite reaction, i.e. a method is provided for the conversion of a cytosine base, preferably cytosine bases, in a nucleic acid to an uracil base, preferably uracil bases, whereby preferably 5-methylcytosine bases are not significantly converted ("bisulfite reaction" or "bisulfite treatment") comprising the steps of a) providing a mixture of a nucleic acid and other biological compounds
b) binding the nucleic acid to a solid phase, optionally removing the other biological compounds and optionally washing the solid phase bound nucleic acid,
c) incubating the nucleic acid in the presence of sulfite ions thereby deaminating the cytosine base in the nucleic acid and optionally washing the solid phase bound nucleic acid,
d) incubating the solid phase bound nucleic acid in a solution with an alkaline pH thereby
desulfonating the cytosine base in the nucleic acid and converting it to an uracil base and
eluting the nucleic acid.

According to the present invention, for washing and binding steps, preferably liquids are used which are suitable for processes in molecular biology, in particular desoxyribonucleic acid (DNA) or ribonucleic acid (RNA) purification processes which make use of the binding of these substances to a solid phase, in particular silica or glass surfaces, more particularly magnetic glass particles under certain conditions. Preferred liquids comprise alcohols and/or ketones or any mixtures thereof with water. Alcohols shall include according to the invention preferably primary, secondary or tertiary alcohols of the general formula R—OH where the R stands for the general formula —($-CH_2$)$_n$—$CH_3$ with n>=0. However, other alcohols can also be used if they are suitable for molecular biology purposes as e.g. glycerol. Particularly suitable are the alcohols isopropanol, ethanol or mixtures thereof with water, preferably a mixture of 80 volume parts of isopropanol with 20 volume parts of water. In another embodiment of the invention the liquid comprises ketones as e.g. acetone. Further, suitable aqueous buffered solutions are used. Buffer systems which are suitable for molecular biology purposes may be found e.g. in Sambrook, J., et al., in "Molecular Cloning: A Laboratory Manual" (1989), Eds. J. Sambrook, E. F. Fritsch and T. Maniatis, Cold Spring Harbour Laboratory Press, Cold Spring Harbour, N.Y. Preferred buffer substances are Tris-hydroxymethylamine (TRIS), phosphate, N-(2-hydroxy-ethyl)piperazine-N'-(2-ethanesulfonic acid) (HEPES), salts thereof or other suitable substances. Additionally, substances may be present which modify the ionic strength of the solution as e.g. NaCl, KCl or $CaCl_2$ or which are metal cation complexing agents as e.g. ethylene-diamine-tetra-acetic acid (EDTA) or the salts thereof.

The method according to the invention further comprises the step of eluting the bound nucleic acid from said solid phase. Then the eluted nucleic acid may be treated enzymatically e.g. amplified. The solution containing the nucleic acid is ready to be used in the amplification reaction after elution and after the solid phase has been removed. Therefore, the nucleic acid is transferred to a new reaction tube containing all reagents necessary for amplification. Optionally, a solution containing all reagents necessary for amplification is added to the suspension of the solid phase and the released nucleic acids. In another embodiment, a solution containing all reagents necessary for amplification is added to the suspension of the solid phase and the bound nucleic acid without elution step whereby an amplification of the nucleic acid on the solid phase is performed. Therefore, in another embodiment of the invention, a method is provided for the amplification of a nucleic acid comprising the steps of a1) binding the nucleic acid to a solid phase and incubating the solid phase bound nucleic acid in the presence of sulfite ions thereby deaminating the cytosine base in the nucleic acid, or a2) incubating the nucleic acid in the presence of sulfite ions thereby deaminating the cytosine base in the nucleic acid and binding the nucleic acid to a solid phase, b) optionally washing the solid phase bound nucleic acid, c) incubating the solid phase bound nucleic acid in a solution with an alkaline pH thereby desulfonating the cytosine base in the nucleic acid and converting it to an uracil base and eluting the nucleic acid, d) amplifying the eluted nucleic acid.

In a preferred embodiment of the invention, the nucleic acid is amplified with the polymerase chain reaction (PCR; EP 0 201 184, EP 0 200 362, U.S. Pat. No. 4,683,202). The amplification method may also be the ligase Chain Reaction (LCR, Wu, D. Y., and Wallace, R. B., Genomics 4 (1989) 560-9 and Barany, F., Proc Natl Acad Sci USA 88 (1991) 189-93; Polymerase Ligase Chain Reaction (Barany, F., PCR Methods Appl 1 (1991) 5-16); Gap-LCR (PCT Patent Publication No. WO 90/01069); Repair Chain Reaction (European Patent Publication No. EP 439 182 A2), 3SR (Kwoh, D. Y., et al., Proc Natl Acad Sci USA 86 (1989) 1173-7; Guatelli, J. C., et al., Proc Natl Acad Sci USA 87 (1990) 1874-8; PCT Patent Publication No. WO 92/08808), and NASBA (U.S. Pat. No. 5,130,238). Further, there are strand displacement amplification (SDA), transciption mediated amplification (TMA), and Qβ-amplification (for a review see e.g. Whelen, A. C., and Persing, D. H., Annu Rev Microbiol 50 (1996) 349-73; Abramson, R. D., and Myers, T. W., Curr Opin Biotechnol 4

(1993) 41-7). Particularly preferred amplification methods according to the invention are the methylation specific PCR method (MSP) disclosed in U.S. Pat. No. 5,786,146 which combines bisulfite treatment and allele-specific PCR (see e.g. U.S. Pat. Nos. 5,137,806, 5,595,890, 5,639,611).

In a preferred embodiment, the method may further comprise the step of detecting the amplified nucleic acid. The amplified nucleic acid may be determined or detected by standard analytical methods known to the person skilled in the art and described e.g. in Sambrook, et al., Molecular Cloning, Cold Spring Harbor University Press (1989), Lottspeich and Zorbas, in "Bioanalytik" (1998), Eds. L. a. Zorbas, Spektrum Akademischer Verlag, Heidelberg, Berlin, Germany, or in Ausubel, F., et al., in "Current protocols in molecular biology" (1994), Eds. F. Ausubel, R. Brent and K. R. E., Wiley & Sons Verlag, New York. There may be also further purification steps before the target nucleic acid is detected e.g. a precipitation step. The detection methods may include but are not limited to the binding or intercalating of specific dyes as ethidium bromide which intercalates into the double-stranded DNA and changes its fluorescence thereafter. The purified nucleic acids may also be separated by electrophoretic methods optionally after a restriction digest and visualized thereafter. There are also probe-based assays which exploit the oligonucleotide hybridization to specific sequences and subsequent detection of the hybrid. It is also possible to sequence the target nucleic acid after further steps known to the expert in the field. Other methods apply a diversity of nucleic acid sequences to a silicon chip to which specific probes are bound and yield a signal when a complementary sequences bind.

In a particularly preferred embodiment of the invention, the nucleic acid is detected by measuring the intensity of fluorescence light during amplification. This method entails the monitoring of real time fluorescence. A particularly preferred method exploiting simultaneous amplification and detection by measuring the intensity of fluorescent light is the TaqMan® method disclosed in WO 92/02638 and the corresponding U.S. Pat. Nos. 5,210,015, 5,804,375, 5,487,972. This method exploits the exonuclease activity of a polymerase to generate a signal. In detail, the nucleic acid is detected by a process comprising contacting the sample with an oligonucleotide containing a sequence complementary to a region of the target nucleic acid and a labeled oligonucleotide containing a sequence complementary to a second region of the same target nucleic acid strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. The format used in the TaqMan® instrument eliminates the need for a solid phase bound reaction complex to be formed and made detectable. In more general terms, the amplification and/or detection reaction of the method according to the invention is a homogeneous solution-phase assay. Further preferred method are the formats used in the LightCycler® instrument (see e.g. U.S. Pat. No. 6,174,670). Particularly preferred is the use of bisulfite treatment, amplification with or without methylation specific primers in the presence of a methylation-specific probe and real-time fluorescence detection as described in U.S. Pat. No. 6,331,393.

In a preferred embodiment of the present invention, the method is automated, i.e. the method carries out an automatable process as e.g. described in WO 99/16781. Automatable process means that the steps of the process are suitable to be carried out with an apparatus or machine capable of operating with little or no external control or influence by a human being. Automated method means that the steps of the automatable method are carried out with an apparatus or machine capable of operating with little or no external control or influence by a human being. Only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. In a preferred embodiment of the invention, the method is in a high-throughput format, i.e. the automated methods is carried out in a high-throughput format which means that the methods and the used machine or apparatus are optimized for a high-throughput of samples in a short time.

Preferably the method according to the invention is used in diagnostics, for diagnostic analysis or for bioanalytics, or for the screening of tissue or fluids from the human or even animal body for the presence of certain methylation pattern. Further, the method according to the invention is used to enhance the speed, accuracy or sensitivity of the detection of methylation sites in nucleic acids.

In an embodiment of the present invention a solution comprising 10 to 100 mM, preferably 20 to 60 mM, NaOH or KOH is used for the desulfonation of a sulfonated and deaminated cytosine base in a nucleic acid or for the desulfonation of a sulfonated and deaminated cytosine base in a solid phase bound nucleic acid and the subsequent elution of the solid-phase bound nucleic acid from the solid phase. Preferably, the solid phase is a material comprising silica or glass. Preferably, the solid phase is a glass fleece or a glass membrane. More preferably, the solid phase is a magnetic glass particle.

In another embodiment, the present invention is directed to a kit for performing a bisulfite reaction comprising a bisulfite salt or a solution comprising bisulfite ions, a solid phase, and solution comprising 10 to 100 mM, preferably 20 to 60 mM, more preferably 25 to 50 mM, NaOH or KOH. Preferably, the solid phase is a material comprising silica or glass. Preferably, the solid phase is a glass fleece or a glass membrane. More preferably, the solid phase is a magnetic glass particle. In another preferred embodiment of the invention a kit of parts is provided which comprises a storage container containing the magnetic glass particles or a suspension thereof according to the present invention. Such kits known in the art further comprise plastics ware which may be used during the bisulfite procedure as e.g. microtiter-plates in the 96 or 384 well format or reaction tubes manufactured e.g. by Eppendorf, Hamburg, Germany. The kit may further comprise a washing solution which is suitable for the washing step of the solid phase, in particular, the glass fleece or membrane or the magnetic glass particles. Often the washing solution is provided as a stock solution which has to be diluted before the use. Further, additional reagents may be present which contain buffers suitable for use in the present invention. Preferably, the kit according to the invention is used for a reaction wherein a cytosine base, preferably cytosine bases, in a nucleic acid is converted to an uracil base, preferably uracil bases, in the presence of bisulfite ions whereby preferably 5-methyl-cytosine bases are not significantly converted.

The following examples are provided to aid the understanding of the present invention, the true scope of which is set forth in the appended claims. It is understood that modifications can be made in the procedures set forth without departing from the spirit of the invention.

EXAMPLE 1

Comparison of Simplified BIS Process and State of the Art Procedure

Example 1

Background

The fact that the bisulfite reaction has worked and converted non-methylated cytosines to uracil can be demonstrated by a polymerase chain reaction whereby primers are used which are specific to a region of the nucleic acid sequence wherein non-methylated cytosines have been converted to uracils, i.e. the base adenine in the primer is opposite to the uracil being the bisulfite reaction product from non-methylated cytosines. In case of incomplete conversion, the primer could not hybridize to this region as there would be cytosines not matching the adenine bases in the primer. This would have the effect that no PCR product would be obtained.

An improved method to perform rapid polymerase chain reactions is disclosed e.g. in U.S. Pat. No. 6,174,670 and is used in the LightCycler® instrument (Roche, Mannheim, Germany). In this method, two labeled probes can come into close proximity in an amplificate dependent manner so that the two labels can perform a fluorescence energy transfer (FRET). The amount of the amplificate thereby correlates with the intensity of the emitted light of a certain wavelength. This specific PCR method can therefore be used to analyze whether a complete conversion of non-methylated cytosines was obtained using suitable probes and primers. However, the expert skilled in the art knows that other methods can be used for this evaluation as well. Fluorescence measurements are normalized by dividing by an initial fluorescence measurement, i.e., the background fluorescence, obtained during a cycle early in the reaction while the fluorescence measurements between cycles appear to be relatively constant. The cycle number chosen for the initial fluorescence measurement is the same for all reactions compared, so that all measurements represent increases relative to the same reaction cycle. In the early cycles of a polymerase chain reaction amplification, the number of target molecules can be described by the geometric equation $N_i = N_o \times (1+E)^i$, where $N_o$=the number of target molecules at the start of the reaction, $N_i$=the number of target molecules at the completion of the i-th cycle, E=the efficiency of the amplification ($0=<E=<1$). During this geometric growth phase of the amplification, the number of cycles required to reach a particular threshold value ($C_T$ or $C_P$ value or crossing point) is inversely proportional to the logarithm of (1+E). Thus, the $C_T$ or $C_P$ value represents a measure of the reaction efficiency that allows comparisons between reactions. A decrease in the $C_T$ or $C_P$ value, which means that the reaction reached the threshold value in fewer cycles, indicates an increase in reaction efficiency. As the increase in amplification product is monitored by measuring the increase in reaction fluorescence, the $C_T$ or $C_P$ is defined herein as the number of amplification cycles carried out until the fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. Accumulation of amplified product in later cycles inhibits the reaction and eventually leads to a reaction plateau. An AFL of 1.5 was chosen for all reactions. Because a PCR amplification consists of discrete cycles and the fluorescence measurements are carried out once per cycle, the measured fluorescence typically increases from below the AFL to above the AFL in a single cycle. To improve the precision of the measurements, an "exact" number of cycles to reach the AFL threshold, referred to herein as the $C_T$ or $C_P$ value or crossing point, was calculated by interpolating fluorescence measurements between cycles.

Example 1

Experiments

After deamination of bisulfite treated DNA (for example extracted from paraffin-embedded tissues (PET tissues) according to standard methods) the solution with deaminated DNA is bound to a solid phase (for example magnetic glass particles) and washed to remove the bisulfite. Then the bisulfite treated DNA is eluted directly using different concentrations of NaOH at various temperatures and used for subsequent amplification (simplified bisulfite process) or the bound bisulfite treated DNA is desulfonated first, then washed again and eluted with TE buffer (as described in the European patent application EP 1 394 173). The composition of the mastermix and the amplification conditions were identical to EP 1 394 173, but the master mix used for the simplified workflow was pH 7.8 vs 8.2 for the reference process resulting in an identical pH of the PCR reaction mix itself. Samples were processed in triplicate and the results are also shown in triplicate. Any PCR using primer/probes specific for bisulfite converted DNA can be used or the Substance and methods described in EP 1 394 173.

The following table shows that the simplified workflow works well in a broad range of NaOH concentrations and at different elution temperatures and is even more sensitive than the reference process.

| Sample treatment Simplified BIS process | Ct values | | |
|---|---|---|---|
| Elution at | Sample 40 | Sample 41 | Sample 42 |
| 50 mM NaOH 60° C. | 34.2 | 29.1 | 30.4 |
|  | 34.7 | 28.0 | 29.7 |
|  | 35.1 | 27.6 | 29.1 |
| mean ct value | 34.7 | 28.2 | 29.7 |
| 40 mM NaOH 60° C. | 34.6 | 27.4 | 28.0 |
|  | 34.0 | 27.4 | 29.8 |
|  | 34.6 | 27.9 | 28.8 |
| mean ct value | 34.4 | 27.5 | 28.9 |
| 40 mM NaOH 80° C. | 35.6 | 27.9 | 32.1 |
|  | 34.9 | 28.4 | 29.8 |
|  | 34.5 | 28.0 | 28.2 |
| mean ct value | 35.0 | 28.1 | 30.0 |
| 25 mM NaOH 60° C. | 33.2 | 27.7 | 28.2 |
|  | 34.3 | 28.1 | 29.4 |
|  | 34.6 | 28.4 | 28.8 |
| mean ct value | 34.0 | 28.1 | 28.8 |
| 25 mM NaOH 80° C. | 34.6 | 28.8 | 27.9 |
|  | 34.2 | 27.4 | 28.3 |
|  | 34.6 | 27.7 | 28.5 |

-continued

| Sample treatment Simplified BIS process | Ct values | | |
|---|---|---|---|
| Elution at | Sample 40 | Sample 41 | Sample 42 |
| mean ct value | 34.4 | 28.0 | 28.2 |
| Reference procedure | 37.1 | 30.4 | 31.6 |
|  | 35.2 | 30.2 | 30.5 |
|  | 35.1 | 29.1 | n.t |
| mean ct value | 35.8 | 29.9 | 31.0 |

EXAMPLE 2

Automation of Simplified BIS Process on the COBAS® AmpliPrep Instrument Using the COBAS® AmpliPrep Total Nucleic Acid Isolation (TNAI) Kit (Roche Diagnostics, Mannheim. Germany)

Deaminated DNA from 2 PET samples was either processed manually (as described above) or automatically by adding water up to 1000 µl and putting the tube to the COBAS® AmpliPrep instrument (Roche Diagnostics, Mannheim, Germany) and applying a programme omitting the proteinase K and internal control pipetting step. Binding buffer, magnetic glass particles (MGPs) and washing buffer from the TNAI kit were used, but the elution reagent was 25 mM NaOH in PCR water. Elution volume was 75 µl. For the automatic method a four fold-determination was performed, for the manual method an eightfold one.

For subsequent amplification 50 µl of eluate resulting from manual or automatic process was amplified.

The following table shows the results: the automated process worked very effective, the Ct values were even better than for the manual process, probably due to more efficient washing process on the COBAS® AmpliPrep instrument.

|  | Ct-values | | | |
|---|---|---|---|---|
|  | Sample 38 | | Sample 40 | |
| Independent Experiments | Automated process | Manual process | Automated process | Manual process |
|  | 30.0 | 36.0 | 34.6 | 34.6 |
|  | 30.1 | 33.2 | 33.3 | 34.8 |
|  | 29.1 | 31.1 | 33.2 | 34.2 |
|  | 29.3 | 33.9 | 32.9 | 34.5 |
|  |  | 33.5 |  | 35.0 |
|  |  | 30.8 |  | 34.4 |
|  |  | 35.1 |  | 34.2 |
|  |  | 32.6 |  | 34.5 |
| Mean Ct-value | 29.6 | 33.3 | 33.5 | 34.5 |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

I claim:
1. A method for the conversion of a cytosine base in a nucleic acid to an uracil base comprising the steps of
   a1) binding the nucleic acid to a solid phase capable of binding nucleic acids and incubating the solid phase bound nucleic acid in the presence of sulfite ions thereby deaminating the cytosine base in the nucleic acid, or
   a2) incubating the nucleic acid in the presence of sulfite ions thereby deaminating the cytosine base in the nucleic acid and binding the nucleic acid to a solid phase,
   b) optionally washing the solid phase bound nucleic acid,
   c) contacting the solid phase bound nucleic acid with a solution with an alkaline pH thereby desulfonating the base deaminated in step a1) or a2) in the nucleic acid and converting it to an uracil base and simultaneously eluting the nucleic acid.
2. The method according to claim 1 wherein the solution with an alkaline pH comprises NaOH or KOH.
3. The method according to claim 1, wherein the solution with an alkaline pH comprises 10 to 100 mM NaOH or KOH.
4. The method according to claim 3, wherein the solution with an alkaline pH comprises 20 to 60 mM NaOH or KOH.
5. The method according to claim 1, wherein the temperature in step c) of the method of claim 1 is between 60 to 80° C.
6. The method according to claim 1, wherein the solid phase is a material comprising silica or glass.
7. The method according to claim 1, wherein the solid phase is a glass fleece or a glass membrane.
8. The method according to claim 1, wherein the solid phase is a magnetic glass particle.
9. The method of claim 8 wherein the magnetic glass particle has a mean diameter between 0.5 µm and 5 µm.
10. The method according to claim 8 wherein the magnetic glass particle contains a magnetic object with a diameter between 5 and 500 nm.
11. A method for the amplification of a nucleic acid comprising the steps of
   a1) binding the nucleic acid to a solid phase capable of binding nucleic acids and incubating the solid phase bound nucleic acid in the presence of sulfite ions thereby deaminating the cytosine base in the nucleic acid, or
   a2) incubating the nucleic acid in the presence of sulfite ions thereby deaminating the cytosine base in the nucleic acid and binding the nucleic acid to a solid phase,
   b) optionally washing the solid phase bound nucleic acid,
   c) contacting the solid phase bound nucleic acid with a solution with an alkaline pH thereby
   desulfonating the base deaminated in step a1) or a2) in the nucleic acid and converting it to an uracil base and simultaneously eluting the nucleic acid,
   d) amplifying the eluted nucleic acid by PCR or related method.
12. A kit for performing a bisulfite reaction comprising
   a bisulfite salt or a solution comprising bisulfite ions,
   a solid phase capable of binding nucleic acids, and
   a solution comprising 10 to 100 mM NaOH or KOH.
13. The kit according to claim 12 wherein the solid phase is a material comprising silica or glass.
14. The kit according to claim 12, wherein the solid phase is a glass fleece or a glass membrane.
15. The kit according to claim 12, wherein the solid phase is a magnetic glass particle.
16. The kit according to claim 12, wherein the solution of NaOH or KOH comprises 20 to 60 mM of NaOH or KOH.

* * * * *